United States Patent [19]

Shibata et al.

[11] Patent Number: 4,882,033
[45] Date of Patent: Nov. 21, 1989

[54] ELECTROCHEMICAL DEVICE

[75] Inventors: Kazuyoshi Shibata; Yoshihiko Mizutani, both of Nagoya, Japan

[73] Assignee: NGK Insulators, Ltd., Nagoya, Japan

[21] Appl. No.: 57,645

[22] Filed: Jun. 8, 1987

Related U.S. Application Data

[63] Continuation of Ser. No. 764,646, Aug. 12, 1985, abandoned.

[30] Foreign Application Priority Data

Aug. 21, 1984 [JP] Japan ................. 59-174530

[51] Int. Cl.[4] ........................................... G01N 27/46
[52] U.S. Cl. .................................. 204/425; 204/426; 204/427; 204/429
[58] Field of Search ......................... 204/1 S, 421–429

[56] References Cited

U.S. PATENT DOCUMENTS

| | | | |
|---|---|---|---|
| 4,207,159 | 6/1980 | Kimura et al. | 204/426 |
| 4,264,425 | 4/1981 | Kimura et al. | 204/429 |
| 4,282,080 | 8/1981 | Muller et al. | 204/428 |
| 4,304,652 | 12/1981 | Chiba et al. | 204/425 |
| 4,384,935 | 5/1983 | DeJong | 204/426 |
| 4,450,065 | 5/1984 | Yamada et al. | 204/412 |
| 4,496,455 | 1/1985 | Linder et al. | 204/425 |
| 4,505,807 | 3/1985 | Yamada | 204/429 |
| 4,559,126 | 12/1985 | Mase et al. | 204/426 |
| 4,568,443 | 2/1986 | Asayama et al. | 204/412 |
| 4,574,627 | 3/1986 | Sakurai et al. | 204/426 |
| 4,655,901 | 4/1987 | Mase et al. | 204/425 |

FOREIGN PATENT DOCUMENTS

| | | |
|---|---|---|
| 0066228 | 12/1982 | European Pat. Off. . |
| 0142993 | 5/1985 | European Pat. Off. . |
| 0100853 | 6/1984 | Japan .................. 204/426 |
| 2050625 | 1/1981 | United Kingdom . |
| 2052761 | 1/1981 | United Kingdom . |

Primary Examiner—T. Tung
Attorney, Agent, or Firm—Arnold, White & Durkee

[57] ABSTRACT

An electrochemical device having a sensing cell and a pumping cell. The sensing cell includes: a first planar solid electrolyte body; a first and a second porous electrode disposed on the first planar solid electrolyte body, the second electrode being exposed to a reference gas which has a predetermined oxygen partial pressure; and a diffusion resistance member which has a predetermined diffusion resistance to a measurement gas and covers the first electrode. An electric current is applied between the first and second electrodes, such that the electric current flows from the first electrode to the second electrode to induce an electrode reaction for controlling an atmosphere adjacent to the first electrode. The pumping cell includes: a second planar solid electrolyte body; a third and a fourth electrode of a porous structure disposed on the second planar solid electrolyte body. The third electrode is exposed to the reference gas to which the second electrode is exposed, and the fourth electrode is exposed to the measurement gas. An electric current is applied to flow from the third electrode to the fourth electrode, whereby an oxygen component of the measurement gas moves into the reference gas.

12 Claims, 4 Drawing Sheets

ELECTROCHEMICAL DEVICE

This is a continuation of application Ser. No. 764,646 filed Aug. 12, 1985, now abandoned.

BACKGROUND OF THE INVENTION

1. Field of the Art

The present invention relates to an electrochemical device, and more particularly to an electrochemical device capable of not only measuring an oxygen partial pressure of a lean-burned exhaust gas, but also detecting an amount of unburned components of a rich-burned exhaust gas.

2. Related Art Statement

There have been known various electrochemical devices, each of which comprises an electrochemical cell using a solid electrolyte body. Such electrochemical devices are used, for example, as oxygen sensors to detect the oxygen concentration of an exhaust gas (combustion exhaust gas) produced by internal combustion engines of automotive vehicles. Typical examples of such oxygen sensors include an oxygen sensor which employs a mass of oxygen-ion conductive solid electrolyte such as zirconia ceramics, to determine he oxygen concentration according to the principle of an oxygen concentration cell. In the field of manufacturing such electrochemical devices, there has been an increasing trend of using an electrochemical cell of a laminar structure which comprises a planar solid electrolyte body and planar electrodes disposed in contact with a surface or surfaces of the planar body of solid electrolyte.

The above-indicated types of electrochemical sensors were originally developed and designed as oxygen sensors for sensing a measurement gas such as an exhaust gas which is produced as a result of combustion of an air-fuel mixture at the stoichiometric air-fuel ratio. Recently, however, it is proposed to use such oxygen sensors as so-called "lean A/F" sensors for sensing a lean-burned exhaust gas which is emitted in combustion of a fuel-lean air-fuel mixture, i.e., as a result of combustion with an excessive amount of air. Namely, the "lean A/F" sensor is capable of detecting the oxygen partial pressure of an oxygen-rich exhaust gas whose oxygen partial pressure is higher than that of the stoichiometric air-fuel ratio.

As a "lean A/F" sensor of such type, an electrochemical device is known, which has an electrochemical sensing cell which comprises: a first planar oxygen-ion conductive solid electrolyte body; a first and a second electrode of porous structure disposed on the first planar solid electrolyte body such that the first and second electrodes are spaced from each other; diffusion resistance means which has a predetermined diffusion resistance to a measurement gas and covers the first electrode so that the first electrode is exposed to the measurement gas diffused through the diffusion resistance means; means for introducing a reference gas having a predetermined oxygen partial pressure, for exposure of the second electrode to the reference gas; and means for applying an electric current between the first and second electrodes, to induce an electrode reaction for controlling an atmosphere adjacent to the first electrode. In this arrangement of the electrochemical device, the oxygen component of the measurement gas which has been diffused toward the first electrode through the diffusion resistance means with its diffusion resistance, is further moved toward the second electrode by means of a pumping action which takes place due to a flow of the electric current between the first and second electrodes. Since a voltage between the two electrode is changed abruptly when the amount of diffusion of the oxygen component corresponding to the oxygen concentration of the measurement gas is changed beyond a given limit, the value of electric current upon abrupt change of the voltage, that is, a limiting current is measured to determine the oxygen concentration (oxygen partial pressure) of the measurement gas.

Problem Solved by the Invention

However, the known lean A/F sensor described above may not be utilized for sensing a rich-burned exhaust gas which is produced as a result of combustion of an air-fuel mixture containing an amount of fuel which is larger than an air-fuel mixture of the stoichiometric ratio, namely, an exhaust gas which contains an amount of unburned combustibles, which has substantially no oxygen partial pressure. In other words, the known lean A/F sensor is not capable of sensing such unburned combustibles in the rich-burned exhaust gas, to detect the combustion condition of an engine emitting the exhaust gas.

Stated in more detail, the measurement of the unburned components of the rich-burned exhaust gas by the conventional lean A/F sensor requires that an electric current between the first and second electrodes be caused to flow in a direction opposite to that in the lean A/F sensor, in order to move the oxygen in the reference gas adjacent to the second electrode, toward the first electrode, so that the unburned combustibles diffused through the diffusion resistance means may be burned as a result of a reaction of the unburned combustibles with the oxygen of the reference gas from the second electrode. Usually, the ambient air is introduced as the reference gas to the second electrode through a suitable reference-gas passage. However, a diffusion resistance of the reference-gas passage may be so large as to restrict the amount of supply of the oxygen from the ambient air to the second electrode, whereby the oxygen supply through the reference-gas passage to the second electrode may not meet the required amount of supply of the oxygen to the first electrode for burning the unburned combustibles. Therefore, the lean A/F sensor fails to sense the unburned components of the rich-burned exhaust gas. Additionally, it has been considered to reduce the diffusion resistance of the reference-gas passage by enlarging its cross sectional area. Practically, however, this solution may not be an effective solution to the above problem, since the sensor is required to be of a compact laminar construction with minimum thickness and width.

SUMMARY OF THE INVENTION

It is accordingly an object of the present invention to provide an electrochemical device which is capable of not only measuring an oxygen partial pressure of a lean-burned exhaust gas, but also detecting an amount of unburned components of a rich-burned exhaust gas.

According to the present invention, there is provided an electrochemical device having an electrochemical sensing cell which includes: a first planar oxygen-ion conductive solid electrolyte body; a first and a second electrode of porous structure disposed on the first planar solid electrolyte body such that the first and second electrodes are spaced apart from each other; diffusion resistance means which has a predetermined diffusion resistance to a measurement gas and covers the first electrode so that the first electrode is exposed to the measurement gas via the diffusion resistance means; means for introducing a reference gas having a predetermined oxygen partial pressure, for exposure of the second electrode to the reference gas; and means for applying an electric current between the first and second electrodes, to induce an electrode reaction for controlling an atmosphere adjacent to the first electrode, the electrochemical device further comprising:

an electrochemical pumping cell comprising: a second planar oxygen-ion conductive solid electrolyte body; a third and a fourth electrode of porous structure disposed on said second planar solid electrolyte body such that the third and fourth electrodes are spaced apart from each other, said third electrode being exposed to an atmosphere that is substantially the same as said reference gas to which said second electrode is exposed, said fourth electrode being exposed to said measurement gas; and means for inducing a flow of electric current from said third electrode to said fourth electrode and thereby supplying an oxygen component of said measurement gas into said reference gas to which said second electrode is exposed.

In the electrochemical device constructed according to the invention as described above, the electrochemical pumping cell functions to supply the oxygen component of the external measurement gas into the reference gas to which the second electrode of the electrochemical sensing cell is exposed. Therefore, the instant electrochemical device is not only able to measure the oxygen partial pressure of a lean-burned exhaust gas (the measurement gas), but is also able to detect an amount of unburned components of a rich-burned exhaust gas (the measurement gas). Described more particularly, the oxygen to be supplied from the measurement gas by the pumping action of the pumping cell will prevent shortage of oxygen in the reference gas even when the oxygen in the reference gas is moved to the first electrode of the sensing cell. Namely, a sufficient amount of oxygen is always supplied from the reference gas on the side of the second electrode, to the side of the first electrode, so that the unburned components of the measurement gas diffused through the diffusion resistance means toward the first electrode may be effectively burned with the oxygen supplied from the reference gas. Moreover, a variation of the electric current between the first and second electrodes is measured to detect the amount of the unburned components included in the measurement gas, whereby the air-fuel (A/F) ratio of an air-fuel mixture that gives the detected amount of unburned components is obtained. That is, the electrochemical device is capable of sensing the combustion condition of an engine which produces the measurement gas.

When the measurement gas is a lean-burned exhaust gas, its oxygen partial pressure is detected by applying an electric current between the first and second electrodes of the sensing cell so as to flow from the second electrode toward the first electrode. This electric current flow causes the oxygen adjacent to the first electrode to move toward the second electrode. As is generally practiced in the art, the limiting current between the two electrodes is measured to detect the oxygen partial pressure of the lean-burned exhaust gas. When the measurement gas is a rich-burned exhaust gas and its unburned components are detected, an electric current is caused to flow in the direction from the first electrode toward the second electrode, so that the oxygen in the reference gas adjacent to the second electrode is moved toward the first electrode. At the same time, the pumping cell operates to feed the oxygen from the measurement gas to the reference gas to which the second electrode is exposed. This pumping action of the pumping cell assures accurate measurement of electric current values which correspond to varying amounts of the unburned components of the specific rich-burned exhaust gases.

As described above, the electrochemical device according to the present invention is capable of detecting unburned components of a rich-burned exhaust gas, as well as of measuring the oxygen partial pressure of a lean-burned exhaust gas. In other words, the present electrochemical device is applicable to any measurement gases which are produced as a result of combustion of air-fuel mixtures of various air-fuel ratios and which may contain varying amounts of unburned components.

According to one advantageous embodiment of the invention, the first and second solid electrolyte bodies of the electrochemical sensing and pumping cells are constituted by a single planar solid electrolyte body.

According to an alternative embodiment of the invention, two planar solid electrolyte bodies are used to serve as the first solid electrolyte body of the sensing cell and the second solid electrolyte body of the pumping cell, respectively. In this case, the second electrode of the sensing cell and the third electrode of the pumping cell may be disposed on opposite sides of an electrically insulating ceramic layer of a porous structure.

In accordance with a further advantageous embodiment of the invention, the first and second electrodes of the sensing cell are disposed on opposite surfaces of the first solid electrolyte body such that the first and second electrodes are aligned with each other.

According to a still further embodiment of the invention, the third and fourth electrodes of the pumping cell are disposed on opposite surfaces of the second solid electrolyte body such that the third and fourth electrodes are aligned with each other.

According to another embodiment of the invention, the second electrode of the sensing cell and the third electrode of the pumping cell are both exposed to a reference-gas passage which communicates with the ambient air.

According to a still another embodiment of the invention, the second electrode of the sensing cell and the third electrode of the pumping cell are constituted by a single layer, or are electrically connected to each other.

In accordance with a further embodiment of the invention, the diffusion resistance means comprises a porous ceramic layer disposed on the first solid electrolyte body so as to cover the first electrode.

In accordance with a still further embodiment of the invention, the diffusion resistance means comprises means for defining a pin hole or thin flat space communicating with an outside space in which the measurement gas exists. The pin hole or thin flat space is open to the outer surface of the first electrode and dimensioned so as to provide the predetermined diffusion resistance.

According to a preferred embodiment of the invention, the electrochemical device further comprises an electric heater layer disposed between the electrochemical sensing and pumping cells. The electric heater layer may be disposed on one side of the electrochemical pumping cell remote from the electrochemical sensing cell.

BRIEF DESCRIPTION OF THE DRAWING

The above and other objects, features and advantages of the present invention will be better understood from the following detailed description of preferred embodiments of the invention, when taken in connection with the accompanying drawing, in which.

DETAILED DESCRIPTION OF THE PREFERRED EMBODIMENTS

To further illustrate the concept of the present invention, several preferred embodiments thereof will be described in detail with reference to the accompanying drawings.

Figure 1:
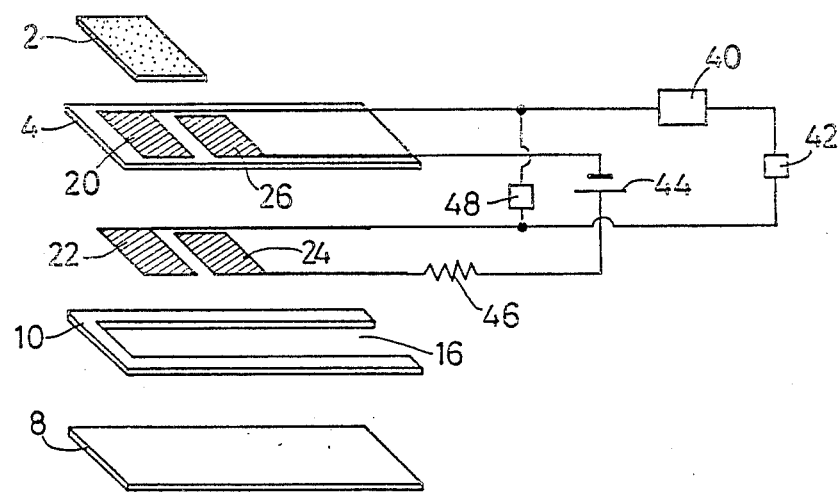
FIGS. 1 and 2 are exploded perspective views of two different embodiments of an electrochemical device of the present invention.

Referring first to FIG. 1, there is shown an example of a basic arrangement of an electrochemical device, wherein a single planar solid electrolyte body is used to form an integral electrochemical assembly which includes an electrochemical sensing cell for determining the concentration of a component of a measurement gas, and an electrochemical pumping cell for performing a pumping action.

Stated more specifically, the electrochemical sensing cell comprises: a planar solid electrolyte body 4 made of a suitable oxygen-ion conductive ceramic material such as zirconia ceramics containing yttria; a first and a second electrode 20, 22 of porous structure made of a platinum-zirconia mixture, which are disposed on opposite surfaces of the solid electrolyte body 4 such that the first and second electrodes 20, 22 are aligned with each other as viewed in the plane of the solid electrolyte body 4; and a porous ceramic layer 2 which has a predetermined diffusion resistance and is disposed so as to cover the first electrode 20. A component of an external measurement gas to be measured is diffused through the porous ceramic layer 2 toward the first electrode 20, whereby the first electrode 20 is exposed to the diffused component of the measurement gas.

The first and second electrodes of the electrochemical sensing cell are connected through their leads to an external DC power source 42, so that an electric current flows in a direction from the first electrode 20 toward the second electrode 22, or in the reverse direction. An ammeter 40 and a voltmeter 48 are provided to measure a current and a voltage across or between the first and second electrodes 20, 22.

The electrochemical pumping cell is formed by providing a third and a fourth electrode 24, 26 of porous structure made for example of a platinum-zirconia mixture, on the opposite surfaces of the above-described solid electrolyte body 4 such that the third and fourth electrodes 24, 26 are aligned with each other. The fourth electrode 26 of this electrochemical pumping cell is disposed on the same surface of the solid electrolyte body 4 as the first electrode 20 of the electrochemical sensing cell. However, the previously indicated porous ceramic layer 2 having the predetermined diffusion resistance does not extend to cover the fourth electrode 26. Instead, the fourth electrode 26 is covered by a protective layer (not shown) which permits the measurement gas (e.g., exhaust gas) to pass therethrough with substantially no diffusion resistance. Thus, the fourth electrode 26 is exposed to the measurement gas. The third and fourth electrodes 24, 26 are connected through their leads to a DC power source 44, so that an electric current flows from the third electrode 24 toward the fourth electrode 26. A reference 46 designates a resistor connected in the pumping cell circuit.

On the side of the common solid electrolyte body 4 for the two electrochemical cells, on which the second and third electrodes 22, 24 is disposed, there are formed a U-shaped spacer member 10 and a covering plate 8 such that the laminated three members 4, 10 and 8 cooperate to define a reference-as passage 16 inside the U-shaped frame of the spacer member 10. The reference-gas passage 16 is held in communication with the ambient air so that the second and third electrodes 22, 24 are exposed to the ambient air in the reference-gas passage.

Figure 2:
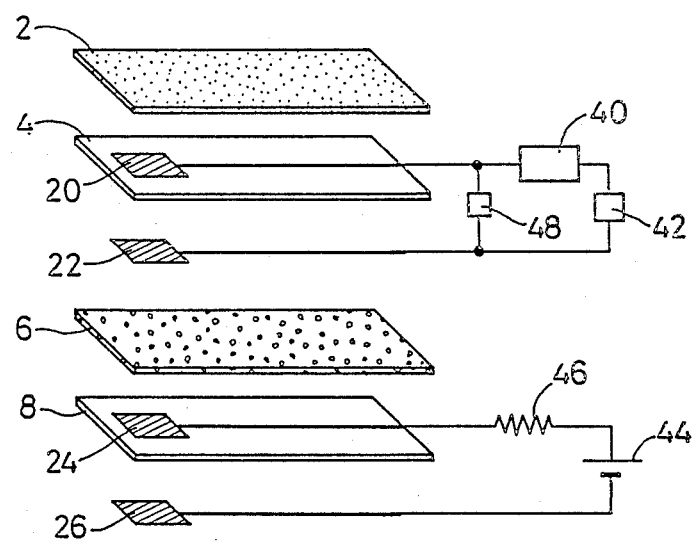

Referring next to FIG. 2, another embodiment of the invention is illustrated. In this embodiment, the electrochemical sensing and pumping cells are disposed on opposite sides of an electrically insulating ceramic layer 6 of a porous structure, such as alumina, which accommodates or holds a reference gas having a predetermined oxygen partial pressure. That is, the instant electrochemical assembly is provided in the form of a co-fired laminar structure in which the insulating porous ceramic layer 6 is sandwiched by the two electrochemical cells.

Obviously, unlike the preceding embodiment, the third and fourth electrodes 24, 26 of the electrochemical pumping cell are disposed on another planar solid electrolyte body 8 which is separate from the solid electrolyte body 4 which is a part of the electrochemical sensing cell. In this embodiment, the fourth electrode 26 of the electrochemical pumping cell and the first electrode 20 of the electrochemical sensing cell are disposed on opposite sides of the laminar structure in the direction of lamination, and the fourth electrode 26 is directly exposed to the external measurement gas.

In the measurement of an exhaust gas as a measurement gas by these electrochemical devices whose basic arrangements have been described above, the exhaust gas may take one of the following three conditions depending upon an air-fuel ratio (A/F) which is a combustion condition of an engine: a neutral atmosphere when the air-fuel ratio is 14.6 (stoichiometric A/F ratio); a lean-burned atmosphere when the air-fuel ratio is greater than the stoichiometric value of 14.6; and a rich-burned atmosphere when the air-fuel ratio is smaller than the stoichiometric value of 14.6.

In the case where the exhaust gas is a lean-burned atmosphere (A/F ratio larger than 14.6), the external DC power source 42 is adapted to cause an electric current to flow in the direction from the second electrode 22 toward the first electrode 20, so that the oxygen in the atmosphere adjacent to the first electrode 20 is moved toward the second electrode 22. Changes in the current and voltage based on an electrode reaction of the measurement component (oxygen) are obtained as limiting currents $I_3$, $I_4$, $I_5$, etc. corresponding to the specific air-fuel ratios of the measurement gas, as is known in the art.

In the case were the exhaust gas is a rich-burned atmosphere (A/F ratio smaller than 14.6), the external DC power source 42 is adapted to cause an electric current to flow in the direction from the first electrode 20 toward the second electrode 22, so that the oxygen in the reference gas is moved from the second electrode 22 toward the first electrode 20. The oxygen moved to the first electrode 20 reacts with and burns the measurement component (unburned combustibles) which have been diffused through the diffusion resistance means in the form of the porous ceramic layer 2, whereby the unburned component is caused to disappear.

Figure 3:
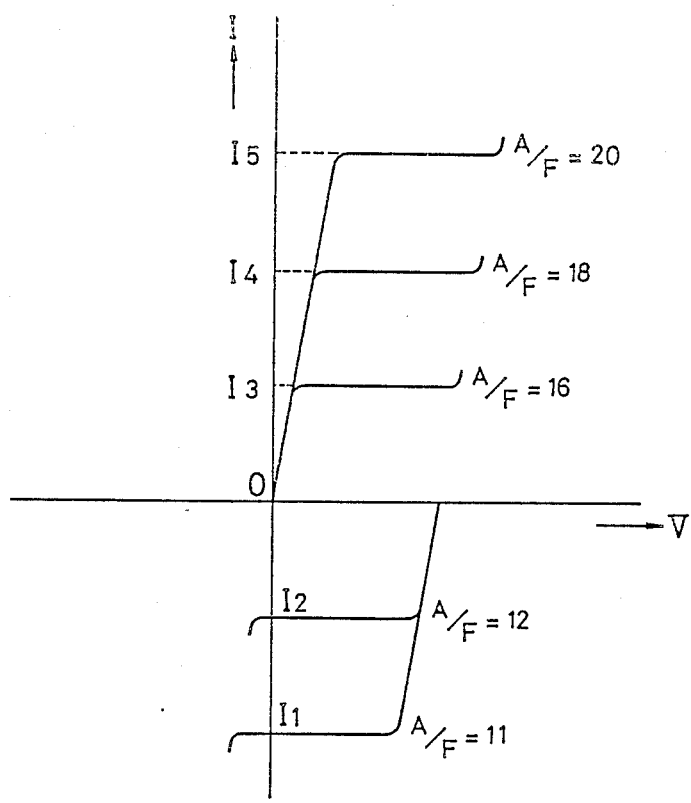
FIG. 3 is a graphical representation of voltage (V)-current (I) relationships which are obtained in measurements of measurement gases by the electrochemical devices of FIGS. 1 and 2.

In the electrode reaction indicated above, the electric current ($I_p$) between the first and second electrodes 20, 22 of the electrochemical sensing cell is gradually increased As shown in FIG. 3, the corresponding voltage drops abruptly when the current $I_p$ is $I_2$ if the A/F ratio is 12. A similar abrupt drop of the voltage occurs when the current $I_p$ is $I_1$ if the A/F ratio is reduced to 11. As described above, the A/F ratios 11 and 12 correspond to electric current values $I_1$ and $I_2$, respectively. Hence, by measuring the electric current $I_p$ ($I_1$, $I_2$), the A/F ratio of the measurement gas may be determined.

During the measurement of the rich-burned exhaust gas, the electrochemical pumping cell of the device is operated with an electric current flowing from the third electrode 24 toward the fourth electrode 26, whereby the oxygen in the measurement gas adjacent to the fourth electrode 26 is moved toward the third electrode 24 and supplied to he reference gas to which the second electrode 22 of the electrochemical sensing cell is exposed. As a result, the second electrode 22 may always be supplied with a sufficient amount of oxygen for correct measurements of the electric current $I_p$($I_1$, $I_2$), even if the reference-gas passage 16 communicating with the ambient air has an excessively high diffusion resistance, or even if the oxygen accommodated within the porous ceramic layer 6 has been consumed.

While the electrochemical pumping cell of the illustrated embodiments is actuated when the measurement gas is a rich-burned atmosphere, it is possible that the pumping cell is operated continuously even while a lean-burned atmosphere is measured. Stated differently, it is not necessary to inhibit the operation of the electrochemical pumping cell when the measurement gas is a lean-burned atmosphere. In the case where the measurement gas is an exhaust gas which is produced as a result of combustion at the stoichiometric air-fuel ratio (A/F =14.6), the measurement may be conducted by detecting an electromotive force induced between the first and second electrodes 20, 22 of the electrochemical sensing cell, as practiced in the conventional electrochemical devices. Further, the measurement is possible by detecting an electromotive force between the third and fourth electrodes 24, 26 of the electrochemical pumping cell.

It is to be understood that the electrochemical device according to the invention is not limited to the illustrated embodiments of FIGS. 1 and 2, but the invention may be otherwise embodied without departing from the scope of the invention. For example, the electrochemical device of the invention may be constructed as shown in FIGS. 4-6.

Figure 4:
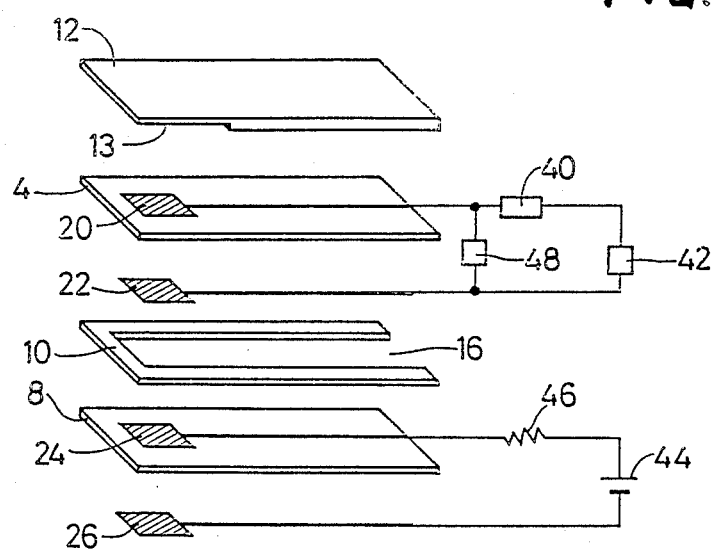
FIGS. 4, 5 and 6 are exploded perspective views of modified arrangements of the electrochemical device according to the invention.

An alternative electrochemical device of FIG. 4 is considered to be a modification of the embodiment illustrated in FIG. 2. Namely, the porous ceramic insulating layer 6 interposed between the two electrochemical cells is replaced by a U-shaped spacer member 10 which cooperates with the upper and lower solid electrolyte bodies 4 and 8 to form a reference-gas passage 16 communicating with the ambient air, so that the second and third electrodes 22, 24 of the electrochemical sensing and pumping cells are exposed to the ambient air in the reference-gas passage 16.

Another difference of the electrochemical device of FIG. 4 from that of FIG. 2 lies in the diffusion resistance means through which the measurement component of the measurement gas is diffused toward the first electrode 20 of the electrochemical sensing cell. Described in more detail, the device of FIG. 4 uses, in place of the porous ceramic layer 2 of FIG. 2, a stepped covering plate 12 which has a recessed portion 13 in the inner surface thereof. This recessed portion 13 and the opposite outer surface of the solid electrolyte body 4 cooperate to define therebetween a thin flat space whose thickness is determined so as to provide a predetermined diffusion resistance to molecules of the measurement component of the measurement gas, so that a predetermined amount of the measurement component of the measurement gas is supplied to the first electrode 20 of the sensing cell.

Figure 5:
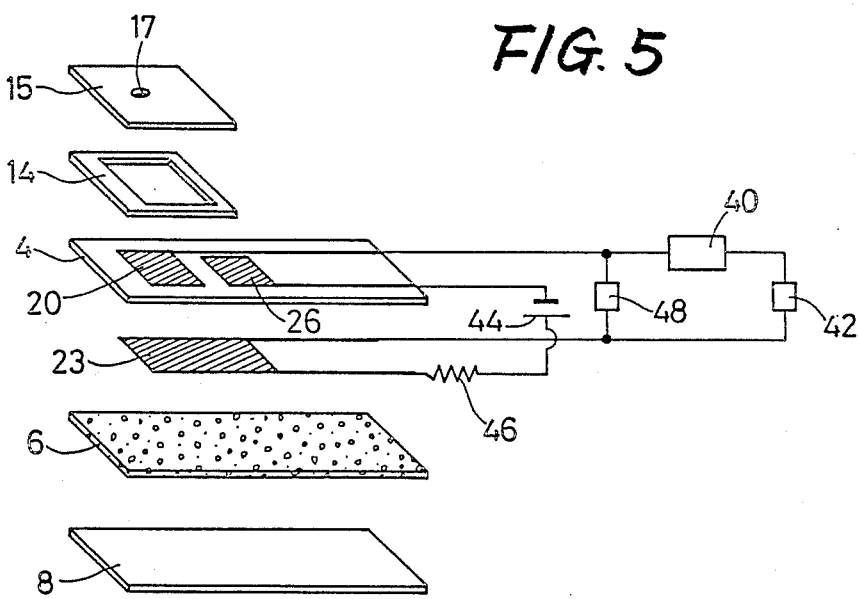
Figure 6:
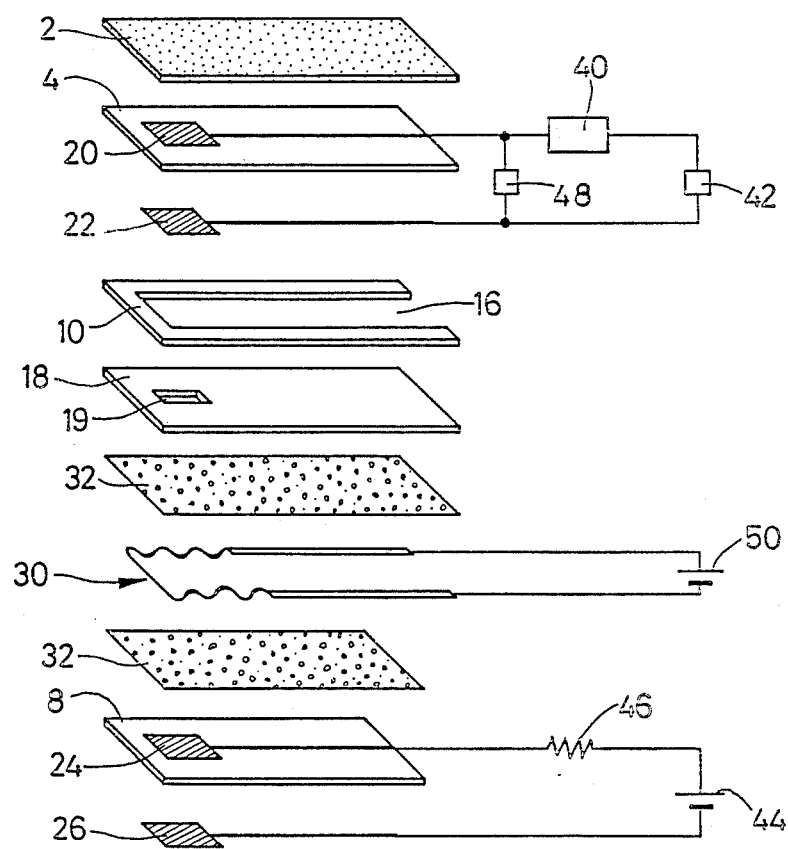

Another alternative embodiment of the invention is illustrated in FIG. 5, which uses another type of diffusion resistance means. This embodiment of FIG. 5 is said to be a modification of the device of FIG. 1. More particularly, the diffusion resistance means having a predetermined diffusion resistance is provided in the form of a pin hole 17 which is formed in a covering plate 15 covering a spacer frame 14 that is disposed so as to surround the first electrode 20.

In this modified diffusion resistance means, the diameter of the pin hole 17 in the covering plate 15 is selected so as to provide a predetermined diffusion resistance to molecules of the measurement component of the measurement gas. That is, the diameter of the pin hole 17 determines the amount of the measurement gas and consequently the amount of the measurement component which is introduced through the pin hole 17 for contact with the first electrode 20.

Unlike the arrangement of FIG. 1, the modified embodiment of FIG. 5 uses an electrode 23 which serves as the second electrode of the sensing cell and the third electrode of the pumping cell. This commonly used electrode 23 is disposed in contact with the electrically insulating porous ceramic layer 6 accommodating a reference gas. The porous ceramic layer 6 is protected from the external measurement gas by the covering plate 8. In this arrangement, the electrode 23 is exposed to the reference gas accommodated in the pores of the porous ceramic layer 6, whereby the second and third electrodes of the electrochemical device are exposed to the substantially same reference atmospheres. The electrode 23 may be replaced by two electrode layers which are electrically connected to each other.

There is illustrated in FIG. 6 a still further modified embodiment of the invention, wherein an electrical heater 30 is disposed between the electrochemical sensing and pumping cells. Described in greater detail, the electrical heater 30 is powered by an external power source 50 (DC power source) to generate heat, and sandwiched between an upper and a lower electrically insulating ceramic layer 32, 32 of a porous structure made of alumina or a similar material. On the assembly of the electrical heater 30 and the insulating ceramic layers 32, 32, there is formed a solid electrolyte substrate 18 of zirconia ceramics or the like, and a U- shaped spacer member 10. The two electrochemical cells are located so as to sandwich these intermediate members, and formed as a laminar structure including these members as integral parts thereof.

With the electrical heater 30 provided between the upper and lower electrochemical cells, the cells are effectively heated, for accurate and reliable operation of the electrochemical device even when the temperature of the measurement gas is relatively low, for example, immediately after a cool engine has just been started.

In the embodiment of FIG. 6, the second electrode 22 of the upper electrochemical sensing cell and the third electrode 24 of the lower electrochemical pumping cell are exposed to substantially the same reference atmospheres, by means of the reference-gas space 16 in the U-shaped spacer member 10, an aperture 19 in the solid electrolyte substrate 18, and the pores in the porous insulating layers 32, 32.

While the electrical heater 30 is located between the two cells in the embodiment of FIG. 6, it is possible that the heater 30 is disposed on the outer side of the electrochemical pumping cell, i.e., so as to cover the fourth electrode 26 of the pumping cell.

While the present invention has been described in detail in its preferred embodiments, it is to be understood that the electrochemical device according to the invention is not confined to the precise disclosure contained herein, but various other changes, modifications and improvements may be made in the invention, which may occur to those skilled in the art, without departing from the spirit of the invention.

Although the solid electrolyte bodies 4, 8 for the electrochemical sensing and pumping cells are preferably made of zirconia ceramics, it is possible to use other oxygen-ion conductive materials such as $SrCeO_3$, and solid solutions of bismuth oxide-oxide of rare earth element. Further, the first, second, third and fourth porous electrodes 20, 22, 24, 26 may be formed of a mixture of an element selected from the platinum group including platinum, palladium, rhodium, iridium, ruthenium and osmium, and an element selected from the ceramic group including zirconia, yttria and alumina. In forming the electrodes, a metal powder mass of the platinum group is admixed with a ceramic powder mass of the ceramic group, and the obtained mixture powder mass is used to form layers in a suitable known manner. The formed layers are fired into the electrodes.

For manufacturing a laminar structure of the electrochemical device including electrochemical sensing and pumping cells and a ceramic heater assembly, various known methods may be practiced. For example, unfired layers of electrodes and their leads, and unfired layers of porous ceramic layers, etc. are formed on green sheets of planar solid electrolyte bodies by a screen-printing technique, and the unfired laminar assembly is co-fired into the co-fired laminar structure.

What is claimed is:

1. An electrochemical device capable of detecting an amount of unburned components in a richburned measurement gas and the partial pressure of oxygen in a lean-burned measurement gas, comprising:

an electrochemical sensing cell which includes (a) a planar oxygen-ion conductive solid electrolyte structure, (b) first and second electrodes of a porous structure disposed on the planar solid electrolyte structure such that the first and second electrodes are spaced apart from each other, (c) diffusion resistance means which has a predetermined diffusion resistance to said rich-burned measurement gas, and diffusion resistance means covering the first electrode such that the first electrode is exposed to the rich-burned measurement gas via the diffusion resistance means, (d) means for introducing a reference gas having a predetermined oxygen partial pressure for exposure of the second electrode to the reference gas, said means for introducing a reference gas having a diffusion resistance that restricts a supply of oxygen to said second electrode during an operation of the device in the rich-burned measurement gas, (e) a DC power source for applying an electric current between said second electrode and said first electrode, said power source being adapted to pass current from said second electrode to said first electrode when the measurement gas is lean-burned for detecting oxygen partial pressure of the measurement gas, and being adapted to pass current from said first electrode to said second electrode when the measurement gas is rich-burned to move oxygen in said reference gas from the second electrode to the first electrode for burning said unburned components of said rich-burned measurement gas which has been diffused to said first electrode through said diffusion resistance means; and an electrochemical pumping cell which includes (a) said planar oxygen-ion conductive solid electrolyte structure, (f) an inner and an outer electrode of a porous structure disposed on said planar solid electrolyte structure such that the inner and outer electrodes are spaced apart from each other, said inner electrode being exposed to an atmosphere that is substantially the same as said reference gas to which said second electrode is exposed, said outer electrode being exposed to said rich-burned measurement gas, and (g) means for inducing a flow of electric current from said inner electrode to said outer electrode and thereby supplying an oxygen component of said rich-burned measurement gas into said reference gas to which said second electrode is expressed, whereby shortage of oxygen in said reference gas is prevented when oxygen in the reference gas moves to said first electrode of the sensing cell, with the electric current flowing from said first electrode to said second electrode.

2. An electrochemical device according to claim 1, wherein said solid electrolyte structure includes a first planar oxygen-ion conductive solid electrolyte body for the electrochemical sensing cell and a second planar oxygen-ion conductive solid electrolyte body for the electrochemical pumping cell.

3. An electrochemical device according to claim 2, wherein said first solid electrolyte body of the electrochemical sensing cell and said second solid electrolyte body of the electrochemical pumping cell are separated from each other by a member made of a material other than a solid electrolyte.

4. An electrochemical device according to claim 3, wherein said second electrode of the electrochemical sensing cell and said inner electrode of the electrochemical pumping cell are disposed on opposite sides of an electrically insulating ceramic layer of a porous structure.

5. An electrochemical device according to claim 2, wherein said first and second electrodes of the electrochemical sensing cell are disposed on opposite surfaces of said first solid electrolyte body such that the first and second electrodes are aligned with each other.

6. An electrochemical device according to claim 2, wherein said inner and outer electrodes of the electrochemical pumping cell are disposed on opposite surface of said second solid electrolyte body such that the inner and outer electrodes are aligned with each other.

7. An electrochemical device according to claim 2, wherein said diffusion resistance means comprises a porous ceramic layer disposed on said first solid electrolyte body so as to cover said first electrode.

8. An electrochemical device according to claim 2, further comprising an electric heater layer disposed at a location selected from the group consisting of between said electrochemical sensing and pumping cells and on one side of the electrochemical pumping cell remote from said electrochemical sensing cell.

9. An electrochemical device according to claim 1, wherein said second electrode of the electrochemical sensing cell and said inner electrode of the electrochemical pumping cell are both exposed to a reference-gas passage which communicates with the ambient air.

10. An electrochemical device according to claim 1, wherein said second electrode on the electrochemical sensing cell and said third electrode of the electrochemical pumping cell are united to form a single layer, of electrically conductive material.

11. An electrochemical device according to claim 1, wherein said diffusion resistance means comprises means for defining a pin hole or thin flat space communicating with an outside space in which said measurement gas exists said pin hole or thin flat space being open to a surface of said first electrode and dimensioned so as to provide said predetermined diffusion resistance.

12. An electrochemical device according to claim 1, wherein said second and inner electrodes are electrically connected to each other.

* * * * *